US008753825B2

(12) United States Patent
Pandian et al.

(10) Patent No.: US 8,753,825 B2
(45) Date of Patent: *Jun. 17, 2014

(54) METHODS AND KITS FOR DETECTING ITA IN A BIOLOGICAL SAMPLE

(75) Inventors: Murugan R. Pandian, Mission Viejo, CA (US); Julie Y. Yu, Mission Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,089

(22) Filed: Jul. 17, 2012

(65) Prior Publication Data

US 2013/0071861 A1 Mar. 21, 2013

Related U.S. Application Data

(60) Continuation of application No. 13/018,182, filed on Jan. 31, 2011, now Pat. No. 8,227,197, which is a continuation of application No. 12/252,282, filed on Oct. 15, 2008, now Pat. No. 7,897,362, which is a continuation of application No. 10/716,739, filed on Nov. 18, 2003, now Pat. No. 7,439,026, which is a division of application No. 09/918,299, filed on Jul. 30, 2001, now abandoned.

(51) Int. Cl.
G01N 33/53 (2006.01)

(52) U.S. Cl.
USPC .............................. 435/7.1; 435/7.2; 436/518

(58) Field of Classification Search
None
See application file for complete search history.

(56) References Cited

U.S. PATENT DOCUMENTS

| | | | |
|---|---|---|---|
| 4,946,958 | A | 8/1990 | Campbell et al. |
| 5,356,817 | A | 10/1994 | Cole |
| 5,506,150 | A | 4/1996 | Canick et al. |
| 5,660,990 | A | 8/1997 | Rao et al. |
| 6,127,186 | A | 10/2000 | Pandian |
| 6,352,862 | B1 | 3/2002 | Davis et al. |
| 6,500,627 | B1 | 12/2002 | O'Connor et al. |
| 6,521,416 | B1 | 2/2003 | Birken et al. |
| 2002/0142305 | A1 | 10/2002 | Chin et al. |
| 2002/0192646 | A1 | 12/2002 | Bellet et al. |
| 2003/0157580 | A1 | 8/2003 | Hochstrasser et al. |
| 2005/0142033 | A1 | 6/2005 | Glezer et al. |
| 2005/0148096 | A1 | 7/2005 | Cole et al. |
| 2011/0201122 | A1 | 8/2011 | Nazareth et al. |

FOREIGN PATENT DOCUMENTS

| | | |
|---|---|---|
| WO | WO-98/10282 | 3/1998 |
| WO | WO-99/41584 | 8/1999 |
| WO | WO-99/56132 | 11/1999 |
| WO | WO-00/42428 | 7/2000 |
| WO | WO-00/70094 | 11/2000 |

OTHER PUBLICATIONS

Kobata et al. Biochimie 1988 vol. 70, p. 1575-1585.*
Cole et al (I). Clin. Chem. 1999 vol. 45, p. 2109-2119.*
Cole et al.(II) Clinical Chem. 2001 vol. 47, p. 308-315.*
Cole, "Hyperglycosylated hCG," Placenta, vol. 28, pp. 977-986, 2007.
Guibourdenche et al., "Hyperglycosylated hCG is a Marker of Early Human Trophoblast Invasion," J. Clin. Endocrino. Metab., vol. 95, No. 10, pp. E240-E244, Oct. 2010.
Strom et al., "The sensitivity and specificity of hyperglycosylated hCG (hhCG) levels to reliably diagnose clinical IVF pregnancies at 6 days following embryo transfer," J. Assist. Reprod. Genet., vol. 29, pp. 609-614, 2012.
International Search Report issued on Mar. 13, 2013 in application No. PCT/US12/71749.
Abushoufa, R.A. et al., "The Development of a sialic acid specific lectin-immunoassay for the measurement of human chorionic gonadotrophin glycoforms in serum and its application in normal and Down's syndrome pregnancies." Clinical Endocrinology 52, 499-508 (2000).
AMS Biotechnology (Europe) Ltd. Monoclonal Antibody to hCG, intact, Purified—E45550M, 2007.
ATCC, The Global Bioresource Center, Product Description, assecion No. hb-12467, Aug. 21, 2007.
ATCC, The Global Bioresource Center, Product Description, assecion No. PTA 1626, Aug. 21, 2007.
Bahado-Singh, R. et al., "A high-sensitivity alternative to 'routine' genetic amniocentesis: multiple urinary analytes, nuchal thickness, and age." Am. J. Obstet. Gynecol. Jan:180(1 pt 1):169-173 (1999).
Bahado-Singh, R.O. et al., "Comparison of urinary hyperglycosylated human chorionic gonadotropin concentration with the serum triple screen for Down syndrome detection in high-risk pregnancies." Am. J. Obstet. Gynecol. Nov;183(5):1114-1118 (2000).
Bahado-Singh, R.O. et al., "New triple screen test for Down syndrome: combined urine analytes and serum AFP." J. Matern. Fetal Med. May-June; 7(3):111-114 (1998).
Biocompare, The Buyer's Guide for Life Scientists, Mouse Anti-hCG, beta Monoclonal Antibody, Unconjugated, Clone 827, Aug. 21, 2007.

(Continued)

Primary Examiner — Jacob Cheu
(74) Attorney, Agent, or Firm — Foley & Lardner LLP

(57) ABSTRACT

Methods for detecting invasive trophoblast antigen (ITA) in biological samples comprise screening the samples for ITA using antibodies that bind to the ITA. The methods are useful to detect pregnancy, trophoblastic diseases, and Down's syndrome in fetuses of pregnant women. Some methods include screening the samples with a plurality of capture antibodies that specifically bind ITA. Chemiluminescent immunoassays are disclosed. The methods may be practiced with the diagnostic kits of the invention.

6 Claims, 8 Drawing Sheets

(56) References Cited

OTHER PUBLICATIONS

Biocompare, The Buyer's Guide for Life Scientists, Mouse Anti-hCG, intact Monoclonal Antibody, Clone 820, 2007.
Birken et al., Immunochemical Measurement of Early Pregnancy Isoforms of HCG: Potential Applications to Fertility Research, Prenatal Diagnosis, and Cancer, Archives of Medical Research Nov.; 32:635-643 (2001).
Birken S. et al., "Development and Characterization of Antibodies to a Nicked and Hyperglocosylated Form of hCG from a Choriocarcinoma Patient." Endocrine, 10:(2) 137-144 Apr. 1999.
Cole, Immunoassay of human chorionic gonadotropin, its free subunits, and metabolites, Clinical Chemistry 43:12 2233-2243 (1997).
Cole, L.A. et al., "Combining beta-core fragment and ottal oestriol measurements to test for Down syndrome . . . " Prenat. Diagn. Dec;17(12):1125-1133 (1997).
Cole, L.A. et al., "Hyperglycosylated hCG, a potential alternative to hCG in Down syndrome screening." Prenat. Diagn. Sep;18(9):926-933 (1998).
Cole, L.A. et al., "Hyperglycosylated Human Chorionic Gonadotropin (Invasive Trophoblast Antigen) Immunoassay: A New Basis for Gestational Down Syndrome Screening." Clinical Chemistry 45:12 2109-2119 (1999).
Cole, L.A. et al., "Urinary screening tests for fetal Down Syndrome: I. Fresh β-core fragment." Prenat. Diagn. Apr;19(4):340-350 (1999).
Cole, L.A. et al., "Urinary screening tests for fetal Down Syndrome: II. Hyperglycosylated hCG." Prenat. Diagn. Apr;19(4):351-359 (1999).
Cole, L.A. et al., "Utility of Commonly Used Commercial Human Chorionic Gonadotropin Immunoassays in the Diagnosis and Management of Trophoblastid Diseases." Clinical Chemistry Feb. 47(2):308-315 (2001).
Cuckle, H.S. et al., "Urinary multiple marker screening for Down's syndrome." Prenat. Diagn. Aug;15(8):745-751 (1995).
Gentaur, Anti-H: pp. 1-13, Aug. 21, 2007.
Google search define: Hydatidiform mole, 2012.
Hsu, J.J. et al., "Urine free beta-hCG and total estriiol for Down syndrome screening during the second trimester in an Asian population." Obstet. Gynecol. Jul; 94(1):107-111 (1999).
Isozaki, T. et al., "Screening for Down syndrome pregnancy using β-core fragment: prospective study." Prenat. Diagn. May;17(5):407-413 (1997).
Kellner, L.H. et al., "Levels of urinary beta-core fragment, total oestriol, and the ratio of the two in second-trimester screening for Down syndrome." Prenat. Diagn. Dec;17(12):1135-1141 (1997).
Krichevsky, A. et al "Development and Characterization of a New, Highly Specific Antibody to the Human Chorionic Gonadotropin-β Fragment." Endocrinology Mar; 128(3):1255-1264 (1991).
Krichevsky, A. et al. "The development of a panel of monoclonal antibodies to human luteinizing hormone and its application to immunological mapping and two-site assays." Endocrine 2:551-520 (1994).
Krichevsky, A. et al., "Development, Characterization, and Application of Monoclonal Antibodies to the Native and synthetic βCOOH-Terminal Portion of Human Chorionic Gonadotropin (hCG) That Distinguishes between the Native and Desialylated Forms of hCG." Endocrinology Mar;134(3):1139-1145 (1994).
O'Conner, J.F. et al., "Differential Urinary gonadotrophin Profiles in Early Pregnancy and Early Pregnancy Loss." Prenat. Diagn. 18:1232-1240 (1998).
Shahabi et al, "Serum Hyperglycosylated hCG: a Potential Screening Test for Fetal Down Syndrome." Prenat. Diagn. 19:488-490 (1999).
Spencer K. et al., "First-trimester urine free beta hCG, beta core, and total oestriol in pregnancies affected by Down's syndrome: implications for first-trimester screening with nuchal translucency and serum free beta hCG." Prenat. Diagn. Jun;17(6):525-538 (1997).
Spencer K. et al., "Urine free beta hCG and beta core in pregnancies affected by Down's syndrome." Prenat. Diagn. Jul;16(7):605-613 (1996).
US Notice of Allowance dated Oct. 28, 2010 in U.S. Appl. No. 12/252,282.
US Notice of Allowance dated Jun. 18, 2008 in U.S. Appl. No. 10/716,739.
US Office Action dated Nov. 12, 2009 in U.S. Appl. No. 12/252,282.
US Office Action dated Jul. 20, 2010 in U.S. Appl. No. 12/252,282.
US Office Action dated Sep. 4, 2007 in U.S. Appl. No. 10/716,739.
US Office Action dated Aug. 22, 2011 in U.S. Appl. No. 13/018,182.
US Office Action dated Dec. 14, 2011 in U.S. Appl. No. 13/018,182.
Notice of Allowance dated Mar. 21, 2012 in U.S. Appl. No. 13/018,182.

* cited by examiner

HYPERGLYCOSYLATED β-SUBUNIT triantennary oligosaccharide

HYPERGLYCOLSYLATED β-SUBUNIT hexasaccharide

METHODS AND KITS FOR DETECTING ITA IN A BIOLOGICAL SAMPLE

SUMMARY OF THE INVENTION

The present invention provides methods for detecting invasive trophoblast antigen (ITA) in a biological sample. In particular, the methods comprise screening biological samples for ITA. One aspect of the invention is related to the discovery that using a combination of two capture antibodies that specifically bind different epitopes of ITA in one assay improves the sensitivity of the assay for the biological marker. Another aspect of the invention is related to the discovery that chemiluminescent immunoassays improve the sensitivity of detection of ITA in biological samples.

In one embodiment of the invention, a method for detecting ITA in a biological sample comprises the step of: contacting a biological sample obtained from a subject with antibodies that bind ITA, in one assay, wherein the assay comprises at least two capture antibodies that specifically bind different epitopes of ITA, and at least one detection antibody that binds an epitope of the ITA distinct from the capture antibody epitopes, and wherein the detection antibody is coupled to a label that produces a detectable signal, wherein the presence of the detectable signal indicates the presence of ITA in the biological sample.

In another embodiment of the invention, a method for detecting ITA in a biological sample comprises contacting the biological sample obtained from a subject with a combination of antibodies that bind ITA in one assay. The assay may comprise at least two capture antibodies that specifically bind different epitopes of ITA, and at least one detection antibody that binds an epitope of the ITA distinct from the capture antibody epitopes. The detection antibody is preferably coupled to a label that produces a detectable signal. The presence of a detectable signal indicates the presence of ITA in the sample.

The assay of the foregoing method may be a chemiluminescent sandwich assay. At least one of the capture antibodies of the sandwich assay may be raised against ITA. Another capture antibody may be raised against hCG or a fragment thereof. In certain embodiments of the invention, the capture antibodies are monoclonal antibodies. For example, the capture antibodies may be monoclonal antibodies designated B152, clone 820, or clone 827 as described herein. In another embodiment of the invention, a combination of capture antibodies designated B152 and clone 820 are used in the methods of the invention. In a further embodiment of the invention, the detection antibody is an antibody, preferably a monoclonal antibody, raised against the beta subunit of hCG. One example of a detection antibody is the monoclonal antibody designated B207.

In another embodiment of the invention, a chemiluminescent immunoassay provides a method for detecting ITA in a biological sample comprising a) contacting the biological sample with a monoclonal capture antibody designated B152 that specifically binds ITA; and b) contacting the biological sample with a monoclonal detection antibody designated B207. In some embodiments, the capture and detection antibodies recognize and bind different epitopes of ITA, and the binding of the detection antibody to the ITA produces a detectable chemiluminescent signal. The foregoing method may also be practiced by screening the biological sample with an additional monoclonal capture antibody designated clone 820.

The signals produced by the foregoing methods may be produced by an acridinium label. In certain embodiments of the invention, the detectable signal produced by the foregoing methods indicates the presence of a trophoblastic disease in the subject.

In another embodiment of the invention, a method for detecting a trophoblastic disease in a subject comprises the steps of a) contacting a biological sample from the subject with antibodies that specifically bind ITA and hCG, in one assay; b) confirming that the subject is not pregnant; and c) comparing the amounts of ITA and hCG in the sample to standard ITA and hCG amounts obtained from a population of normal subjects. A higher amount of ITA and hCG in the sample as compared to the standards indicates the presence of a trophoblastic disease.

In further embodiments of the invention, the trophoblastic disease is choriocarcinoma. In additional embodiments of the invention, the trophoblastic disease is a hydatidiform mole.

The biological samples used in the foregoing methods may be liquid samples or tissue samples. Examples of liquid samples include urine and serum samples.

The assays of the foregoing methods may be automated.

In another embodiment of the invention, a diagnostic kit used to practice the foregoing methods comprises a) a capture antibody solution, wherein the capture antibody solution comprises a plurality of capture antibodies that specifically bind to different epitopes of ITA; and b) a detection antibody solution, wherein the detection antibody solution comprises an antibody that binds ITA and is coupled to a label.

In a further embodiment of the invention, a diagnostic kit comprises a) a plurality of reagent containers; b) a capture antibody solution in one container, wherein the capture antibody solution comprises at least one antibody that specifically binds ITA; and c) a detection antibody solution in one container, wherein the detection antibody solution comprises an antibody that binds ITA and is coupled to a chemiluminescent label.

The capture antibody solution of the foregoing kits may comprise antibodies that specifically bind to different epitopes of the ITA. Examples of some capture antibodies are monoclonal antibodies designated B152, clone 820, and clone 827, as described herein. In certain embodiments of the invention, the capture antibody solution comprises a combination of the B152 and clone 820 monoclonal antibodies, or a combination of the B152 and clone 827 monoclonal antibodies.

The detection antibody solution of the diagnostic kits of the invention may comprise a detection antibody that binds the beta subunit of ITA. One example of a detection antibody is a monoclonal antibody designated B207. In certain embodiments of the invention, the label coupled to the detection antibody used in the diagnostic kits of the invention is a colored particle. In other embodiments, the label is a chemiluminescent compound. The foregoing diagnostic kits may also comprise a luminometer to measure a signal produced by the chemiluminescent label.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE FIGURES

FIG. 1 illustrates N-linked and O-linked oligosaccharides on ITA found in Down's syndrome.

DETAILED DESCRIPTION OF THE INVENTION

Figure 1A:
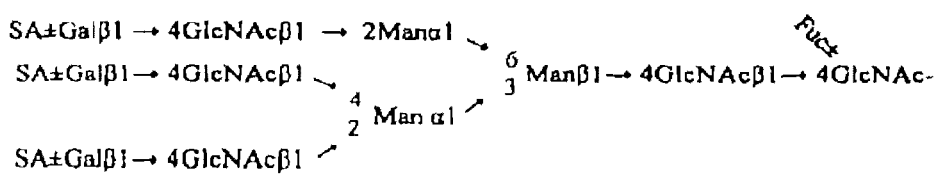
FIG. 1A shows the N-linked hyperglycosylated β-subunit.
Figure 1B:
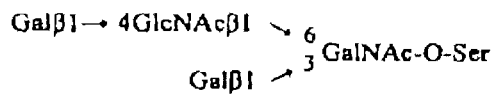
FIG. 1B shows the O-linked hyperglycosylated β-subunit. Abbreviations are as follows: SA sialic acid; Gal for galactose; GlcNAc for N-acetylglucosamine; Man for manose; and Fuc for fucose.

Unless defined otherwise, all technical and scientific terms used herein have the same meaning as commonly understood by those of ordinary skill in the art to which this invention belongs. For purposes of the present invention, the following terms are defined below.

As used herein, "invasive trophoblast antigen" (ITA) is a glycoprotein hormone secreted by trophoblast cells of the placenta of pregnant women. ITA is also called hyperglycosylated hCG. ITA is similar, to C5 hCG, which is a nicked h-hCG obtained from a choriocarcinoma patient. ITA, as defined, also includes fragments of ITA, or variants of ITA. In particular, ITA encompasses molecules that exhibit similar biological activities or expression patterns to ITA and that exhibit aberrant carbohydrate levels as compared to normally glycosylated hCG including, nicked hCG, α-subunits of hCG, β-subunits of hCG, or any combination thereof. Examples of ITA isoforms include isoforms that comprise 57% triantennary N-linked oligosaccharides and 68% hexasaccharide-type O-linked oligosaccharides. Another ITA isoform may comprise 48% triantennary N-linked oligosaccharides and 100% hexasaccharide-type O-linked oligosaccharides. In normal pregnancies, a relatively small proportion of more complex triantennary N-linked oligosaccharides (0-30%) and larger hexasaccharide-type O-linked sugar units (0-20%) are also found.

In one embodiment of the invention, ITA comprises fragments of ITA. For example, greater nicking is observed in ITA preparations compared to hCG preparations. For example, ITA may be nicked or cleaved at similar sites on its beta subunit, and dissociate to form a free alpha subunit and a nicked free hyperglycosylated beta-subunit. Nicked free beta-subunit of ITA can be further degraded to a beta-subunit core fragment comprising short disulfide-linked peptides, with traces of hyperglycosylation sugar moieties.

As used herein, "antibody" refers to a polypeptide substantially encoded by an immunoglobulin gene or immunoglobulin genes, or fragments thereof, which specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques.

An antibody "specifically binds to" or "is immunoreactive with" a protein when the antibody functions in a binding reaction with the protein. In order for the antibody to bind to a protein, the protein should contact the antibody. Accordingly, contacting a sample suspected of containing an antigen of interest with an antibody to the antigen will permit the antibody to specifically bind the antigen. The binding of the antibody to the protein permits determination of the presence of the protein in a sample in the presence of a heterogeneous population of proteins and other agents. Thus, under designated immunoassay conditions, the specified antibodies bind preferentially to a particular protein and do not significantly bind to other proteins present in the sample. Specific binding to a protein under such conditions requires an antibody that is selected for specificity for a particular protein. Several methods for determining whether or not a peptide is immunoreactive with an antibody are known in the art.

As used herein, a "capture antibody" is defined as an antibody, preferably a monoclonal antibody (mAb), attached to a substrate, such as a solid substrate. The capture antibody is selected to specifically bind a particular, distinct epitope of an antigen, such as ITA or hCG.

As used herein, a "capture antibody solution" is defined as a solution containing a combination of two or more capture antibodies that specifically bind different epitopes of an antigen, such as ITA. As disclosed herein, the solution can be in a liquid or solid phase. For example, when the methods of the invention are practiced using wells of a microtiter plate or a cuvette, the capture antibody solution preferably is in a liquid phase. When the methods of the invention are practiced using solid substrates such as nylon or nitrocellulose membranes, the capture antibody solution can be applied in liquid phase to the membrane and allowed to dry thereon. In such embodiments, the capture antibody solution may become solubilized when practicing the methods of the invention, as discussed herein.

As disclosed herein, one capture antibody is designated B152, and may be attached to a solid substrate comprising magnetic particles. Monoclonal antibody B152 specifically binds ITA. The hybridoma producing the B152 monoclonal antibody was deposited on Feb. 3, 1998 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The hybridoma was accorded ATCC Accession Number HB-12467. The B152 antibody was raised against C5 hCG, as disclosed in WO 98/10282, Prenatal Screening for Down's Syndrome Using Hyperglycosylated Gonadotropin; Cole et al., (1998) Hyperglycosylated hCG, a Potential Alternative to hCG in Down Syndrome Screening, Prenatal Diagnosis, 18:926-933; Cole et al., (1999) Hyperglycosylated Human Chorionic Gonadotropin (Invasive Trophoblast Antigen) Immunoassay: A New Basis for Gestational Down Syndrome Screening, 45:2109-2119. Hybridomas producing the B152 monoclonal antibody were obtained from Columbia University.

Another capture antibody used to practice the methods of the invention is the publicly available monoclonal antibody clone 820 available from Biodesign International, Saco, Me. (Catalog Number E45550M). Clone 820 is a monoclonal antibody to hCG. Clone 820 specifically binds to intact hCG (cross reactivity is 100%). The cross reactivity with beta-hCG is less than 1.0%, with alpha-hCG is less than 1.0%, with luteinizing hormone is less than 0.1%, with thyroid stimulating hormone is less than 0.1%, and with follicle stimulating hormone is less than 1.0%. However, as described in Example 2, infra, Clone 820 may also specifically bind ITA, because the ITA standards described herein were reactive with the Clone 820. Clone 820 was produced in mouse, and is an IgG1 isotype. The hybridoma was prepared by fusing myeloma cells with spleen cells from Balb/c mice. Purified Clone 820 is stored in liquid format at a concentration of 5.64 mg/mL in 0.015 M potassium phosphate buffer, 0.15 M NaCl, at a pH of 7.2. The preservative is 0.1% sodium azide.

Another capture antibody used to practice the methods of the invention is the publicly available monoclonal antibody clone 827 available from Biodesign International, Saco, Me. (Catalog Number E45575M). Clone 827 is a monoclonal antibody to the beta subunit of hCG. Clone 827 specifically binds to beta-hCG (cross reactivity is 100%). The cross reactivity with intact hCG is 0.5%, with alpha-hCG is less than 0.1%, with luteinizing hormone is less than 0.1%, with thyroid stimulating hormone is less than 0.1%, and with follicle stimulating hormone is less than 0.1%. However, as described in Example 3, infra, Clone 827 may also specifically bind ITA, because the ITA standards used herein were reactive with the Clone 827. Clone 827 was produced in mouse, and is an IgG1 isotype. The hybridoma was prepared by fusing myeloma cells with spleen cells from Balb/c mice. Purified Clone 827 is stored in liquid format at a concentration of 4.44 mg/mL in 0.015 M potassium phosphate buffer, 0.15 M NaCl, at a pH of 7.2. The preservative is 0.1% sodium azide.

As used herein, a "detection antibody" is defined as an antibody, preferably a monoclonal antibody, that binds an antigen at a binding site or epitope distinct from that of the capture antibody. As is understood in the art, depending on the amount of cross-reactivity that is desired for related antigens, the specificity of the detection antibody may vary. For example, and as discussed herein, for combination assays where two or more antigens are assayed, it may be desirable to use two capture antibodies that specifically bind each antigen, and one detection antibody that will bind an epitope similar or identical on both antigen molecules.

As used herein, a "detection antibody solution" is defined as a solution containing at least one detection antibody that binds an antigen, such as ITA. The detection antibody may bind the antigen at an epitope that is not bound by the capture antibodies. As disclosed herein, the solution can be in a liquid or solid phase. For example, when the methods of the invention are practiced using wells of a microtiter plate or a cuvette, the detection antibody solution may be in a liquid phase. When the methods of the invention are practiced using solid substrates such as nylon or nitrocellulose membranes, the detection antibody solution can be applied to the membrane and allowed to dry thereon.

In certain embodiments of the invention, the detection antibody is a monoclonal antibody that recognizes the beta subunit of hCG and/or the beta subunit of ITA. One example is a monoclonal antibody designated B207. Monoclonal antibody B207 was generated to the beta subunit of hCG, but is cross reactive with the beta subunit of ITA. The hybridoma producing the B207 monoclonal antibody was deposited with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The hybridoma was accorded ATCC Accession Number PTA 1626. The B207 mAb was developed and described in Krichevsky et al., (1994) The Development of a Panel of Monoclonal Antibodies to Human Luteinizing Hormone and its Application to Immunological Mapping and Two-Site Assays, Endocrine, 2:511-520; WO 99/41584, Methods for Predicting Pregnancy Outcome in a Subject by hCG Assay; and WO 00/70094, Methods for Predicting Pregnancy Outcome in a Subject by hCG Assay; O'Connor et al., (1998) Differential Urinary Gonadotrophin Profiles in Early Pregnancy and Early Pregnancy Loss, Prenatal Diagnosis, 18:1232-1240. The hybridoma for the B207 mAb was obtained from Columbia University.

The detection antibody may be coupled to a label, as described herein. The concentration of detection antibody used in practicing the methods of the invention is predetermined and optimized by conducting experiments to determine amounts of detection antibodies that are needed to provide a detectable signal. It will be understood by persons skilled in the art that a sufficient concentration of detection antibody is provided to ensure binding of the detection antibody to all, or essentially all, of the test antigen molecules. In other words, it is preferable to use as much detection antibody as possible without increasing non-specific binding of the detection antibody in the assay to improve the signal-to-noise ratio in practicing the methods of the invention.

In certain embodiments of the invention, capture antibodies are monoclonal antibodies that specifically bind two different epitopes of an antigen. For example, the two capture antibodies may bind an epitope on the beta subunit of ITA, and an epitope on the alpha subunit of ITA. Alternatively, the two capture antibodies may bind different epitopes on the beta subunit of ITA. Additionally, the two capture antibodies may bind an epitope on the alpha subunit and an epitope on the beta subunit of hCG. For ITA, examples of capture antibodies include, but are not limited to, monoclonal antibodies B152, clone 820, and clone 827, as described herein. For other antigens, other antibodies may be produced and screened using conventional immunological techniques. In addition, the detection antibodies may be monoclonal antibodies that bind the antigen at an epitope that does not interfere with the binding of the capture antibodies to the antigen. The detection antibodies can be relatively less specific than the capture antibodies. For example, the detection antibodies can cross react with another antigen that is antigenically similar to the first antigen. One example would be a detection antibody that binds an epitope on the beta subunit of hCG, and an epitope on the beta subunit of ITA. In one embodiment of the invention, the detection antibody is designated B207, as described herein. However, in alternative embodiments of the invention, it is possible to utilize the B207 mAb as the capture antibody, and the B152 mAb, the clone 820 mAb, or the clone 827 mAb as the detection antibody.

A "label" is a composition detectable by spectroscopic, photochemical, biochemical, immunochemical, or chemical means. In other words, a label produces a detectable signal in practicing the methods of the invention. For example, useful labels include fluorescent dyes, chemiluminescent compounds, radioisotopes, electron-dense reagents, enzymes, colored particles, biotin, or dioxigenin. A label often generates a measurable signal, such as radioactivity, fluorescent light, color, or enzyme activity, which can be used to quantitate the amount of bound label.

Examples of chemiluminescent compounds include luciferin, a luminol derivative, pyrogallol, isoluminol, aequorin, cyclic arylhydrazides, dioxetanes, rhodium chelates (electrochemiluminescent), oxalate esters, thermochemiluminescent labels, acridinium and the like. These labels may be attached to a protein, for example an anti-ITA antibody, using techniques well known in the art. (See U.S. Pat. No. 5,284,952, the disclosure of which is incorporated in its entirety herein by reference.) In one embodiment, a detection antibody, such as B207, may be labeled with an acridinium ester by employing the methods found in U.S. Pat. Nos. 5,284,952, 5,110,932, and 5,338,847, the disclosures of which are incorporated in their entirety herein by reference.

Examples of the fluorescent material to be used for labeling include fluorescein, fluorescamine, fluorescein isothiocyanate, umbelliferone, rhodanine, Texas red dyes, pthalocyanines, coumarin, squaraine, anthracene, erythrosine, europium chelates and the like.

Examples of radioactive isotopes to be used for labeling include $^{14}C$, $^{3}H$, $^{32}P$, $^{18}F$ or $^{125}I$.

Exemplary enzymes which have been developed and can be used in assays of the invention are those described in U.S. Pat. Nos. 3,654,090; 3,791,932; 3,839,153; 3,850,752; 3,817,837; 3,879,262; Journal of Immunological Methods 1: 247 (1972); and the Journal of Immunology 109:129 (1972), the disclosures of which are incorporated in their entirety herein by reference. Other examples of enzymes include, but are not limited to, alkaline phosphatase, beta galactosidase, horseradish peroxidase, gluconidase, phosphatase, peptidase, alkaline phosphatase and the like. Co-enzymes useful in this invention include molecules and/or proteins which facilitate an enzyme to catalyze a reactant to produce a detectable product, for example light. A co-enzyme may include, without limitation, FAD and NAD.

Examples of colored particles include colloidal gold, or blue latex.

Other labels may include a non-active precursor of a spectrophotometrically-active substance (British Pat. No. 1,392,403 and French Pat. No. 2,201,299, which patents correspond to U.S. Pat. No. 3,880,934) and electron spin resonance moieties (U.S. Pat. No. 3,850,578).

As described herein, certain parameters of the assays used to practice the methods of the invention are determined prior to practicing the methods of the invention. For example, the components of the solutions and their concentrations (e.g., the concentrations of capture and detection antibodies); the experimental conditions of the assays, such as buffer solution, pH, ionic strength, temperature, incubation times, solid phase support; the coupling chemistry between the support and the various antibodies, and the coupling chemistry between the detection antibody and the label, are preferably predetermined by conducting conventional experiments to optimize the methods of the invention.

As used herein, "normal pregnancy" is defined as a pregnancy wherein the cells of a fetus do not have an excessive amount of chromosomal material, for example, the cells of the fetus do not have an extra copy, or extra part, of chromosome 21.

As used herein, a "pregnancy marker" is defined as a molecule that has an expression pattern or biological activity related to pregnancy. Pregnancy markers include ITA, hCG, and fragments thereof. Other examples of pregnancy markers include, but are not limited to, beta-subunit hCG, beta-core hCG, unconjugated estriol (UE3), alpha-fetoprotein (AFP), leptin, prorenin, renin, DHEA-S, leukocyte acid phosphatase, inhibin, pregnancy associated plasma protein A (PAPP-A), AFP-L3, P43, superoxide dismutase (SOD), proMBP, fetal DNA, insulin-like growth factor binding proteins 3 (IG-FBP3), CA 125, placental lactogen, Hp2FF, serum sialytransferase, s100b protein, schwangers chafts protein 1 (SPI), activin A/follistatin, fetal antigen (FA-2), and placental alkaline phosphatase (PALP). The presence of a pregnancy marker in an immunoassay for pregnancy of a woman indicates that the woman is probably pregnant. The absence of a pregnancy marker in an immunoassay for pregnancy indicates that the woman is probably not pregnant. However, additional queries may be needed to ensure that the absence of a pregnancy marker is not due to a false negative result of the immunoassay. For example, the subject could be asked whether she might be pregnant. Other methods of confirming that the woman is not pregnant would be well understood by those skilled in the art.

As used herein, a "normal subject" is defined as a subject that does not have a trophoblastic disease. Accordingly, normal subjects do not have increased levels of ITA or hCG, or fragments thereof associated with such diseases.

As used herein, a "trophoblastic disease" is a disease associated with abnormal or neoplastic growth of the chorion. Trophoblastic diseases include conditions such as hydatidiform mole, invasive mole, choriocarcinoma, placental site trophoblastic tumor. Hydatidiform mole is defined abnormal growth or cysts of the chorion.

The present invention is, in part, based upon the discovery that an antigen, such as ITA, may be detected in biological samples with increased sensitivity and accuracy by screening the samples with a combination of antibodies, as disclosed herein. The methods of the invention enable one to determine whether a woman is pregnant, whether a pregnant woman has an increased risk of carrying a Down's syndrome fetus, or whether a woman has a trophoblastic disease.

Although one embodiment of the invention is disclosed with respect to ITA, the combination assays disclosed herein can be useful for any antigen that can be detected in an immunoassay. Examples of other antigens that can be used in practicing the methods of the invention include adrenocorticotrophin hormone, calcitonin, parathyroid hormone, human growth hormone, follicle stimulating hormone, luteinizing hormone, prolactin, and/or thyroid stimulating hormone. As described herein, the methods of utilizing two different capture antibodies that specifically bind different epitopes of an antigen may surprisingly improve the sensitivity of the immunoassays so conducted.

The methods for detecting ITA disclosed herein comprise screening biological samples for ITA. In one embodiment, the methods comprise contacting the samples with a plurality of (at least two) capture antibodies that specifically bind different epitopes of the ITA. In addition, the methods may be practiced using chemiluminescent immunoassays. Furthermore, the methods can be practiced by screening samples for ITA and at least one additional analyte or marker, such as, hCG. The concentration of ITA, or other analytes or markers, such as hCG, may then be compared to standards obtained from a population of women who are not pregnant, or women who had normal pregnancies, or women who do not have a trophoblastic disease. The particular standard chosen will be determined based on the condition being screened. Increased levels of ITA, or other analytes, compared to the standards would be indicative that a woman is pregnant, that a fetus has Down's syndrome, or that a woman has a trophoblastic disease.

Biological samples useful for practicing the methods of the invention include, but are not limited to, liquid samples, such as, whole blood, serum, urine, plasma, and amniotic fluid. In addition, the samples may include tissue samples, such as, for example, tissue from the placenta, vagina, or uterus of a pregnant woman. In one embodiment, the liquid sample is urine or serum. In another embodiment, the tissue sample is uterine tissue.

Elevated urine or serum ITA, hCG, or hCG fragment, levels are believed to be markers for pregnancy, Down's syndrome, or trophoblastic diseases. For example, threshold values of hCG for pregnancy are in the range from about 25 mIU/mL to about 100 mIU/mL (IU means International Units; 25 mIU/mL corresponds to approximately 1.79 ng/mL of hCG). Thus, the hCG concentration is typically an indication that the woman being tested is pregnant. It is believed that ITA levels increase before the increase in hCG levels. Thus, measuring the concentration of ITA in a biological sample provides a marker to detect pregnancy before hCG levels increase. Threshold values of ITA for Down's syndrome may be in the range from about 10 ng/mL to about 100 ng/mL; and more preferably are in the range from about 50 ng/mL to about 100 ng/mL. In subjects with trophoblastic disease, hCG levels can be about 2,000,000 ng/mL. ITA concentrations may be about 400,000 ng/mL (i.e., 20% of hCG levels), or may be about 800,000 ng/mL (i.e., 40% of hCG levels) in persistent cases. Free beta hCG concentration may be about 200,000 ng/mL (i.e., 10% of hCG levels). Accordingly, the detection threshold of a particular assay will depend on the condition being assayed.

Depending on the condition being screened, biological samples may be either obtained from the pregnant woman during the first trimester of pregnancy (from about 1 to about 13 weeks) or during the second trimester of pregnancy (from about 13 to about 27 weeks). For example, in a pregnancy screen, a sample may be obtained during the first week after insemination or implantation. In a Down's syndrome screen, the sample is preferably obtained during the second trimester; however, the sample can be obtained during the first trimester as well. Samples may be obtained from pregnant women by any conventional method known to those skilled in the art. For example, serum samples may be obtained by withdrawing a volume of blood from the pregnant woman using conventional intravenous techniques. Amniotic samples can be obtained by withdrawing amniotic fluid from pregnant women using a needle and syringe. Urine samples can be obtained from the pregnant woman. Tissue samples may be taken using conventional techniques, such as, tissue swabs or biopsies. The biological samples, including serum, can be stored before exposing the sample to an assay used to practice the methods of the invention. In practicing the methods of the invention, serum samples may be stable for about three days at room temperature (about 21 degrees C.), for about seven days at about 4 degrees C.; and for about three years at about −60 degrees C.

Screening the biological sample for ITA may be performed by exposing the sample to antibodies that specifically bind ITA.

In one embodiment of the invention, "sandwich" type immunoassays are utilized to measure ITA in a sample. The methods of the invention may utilize a capture antibody that specifically binds ITA. The capture antibody may be coupled to a solid substrate or solid phase. Examples of suitable substrates include, but are not limited to, nylon or nitrocellulose membranes, or wells of microtiter plates or cuvettes. In one embodiment of the invention, the capture antibodies are coupled to paramagnetic particles in cuvettes. For example, biotin-coupled capture antibodies can couple to streptavidin coated paramagnetic particles via the well known avidin-biotin binding reaction. Other methods of coupling the capture antibody to the solid phase of the assays are known to those skilled in the art. In one embodiment of the invention, the capture antibody is designated B152. The B152 monoclonal antibody specifically binds ITA, as described in WO 98/10282, Prenatal Screening for Down's Syndrome Using Hyperglycosylated Gonadotropin; WO 99/41584, Methods for Predicting Pregnancy Outcome in a Subject by hCG Assay; WO 00/70094, Methods for Predicting Pregnancy Outcome in a Subject by hCG Assay; O'Connor et al., (1998) Differential Urinary Gonadotrophin Profiles in Early Pregnancy and Early Pregnancy Loss, Prenatal Diagnosis, 18:1232-1240; Cole et al., (1999) Hyperglycosylated Human Chorionic Gonadotropin (Invasive Trophoblast Antigen) Immunoassay: A New Basis for Gestational Down Syndrome Screening, Clinical Chemistry, 45:2109-2119; Cole et al., (1999) Urinary Screening Tests for Fetal Down Syndrome: II. Hyperglycosylated hCG, Prenatal Diagnosis, 19:351-359; and Shahabi et al., (1999) Serum Hyperglycosylated hCG: a Potential Screening Test for Fetal Down Syndrome, Prenatal Diagnosis, 19:488-490.

In certain embodiments of the invention, the sandwich immunoassays are preferably chemiluminescent immunoassays. The range of sensitivity of ITA concentration of the assays disclosed herein is from about 1 to about 300 ng/mL, but sensitivities of about 0.1 ng/mL are also encompassed. The chemiluminescent assays provide increased sensitivity to current assays used to detect ITA in biological samples.

After screening the sample for ITA, the measured value of ITA is compared to a standard. With respect to pregnancy, the standard may be obtained from a population of women who are not pregnant. With respect to Down's syndrome, the standard may be obtained from a population of pregnant women who had normal pregnancies. In other words, the pregnant women of the population had normal fetuses, or in particular, the fetuses did not have an extra copy or extra amount of chromosome 21. With respect to trophoblastic disease, the standard may be obtained from normal subjects, e.g., subjects that do not have a trophoblastic disease and that are not pregnant.

The ITA can be measured as a concentration (e.g., ng/mL) or as a multiple of medians (MoM). The ITA measured in a sample can be compared to the $50^{th}$ percentile of the ITA values for a population of normal pregnant women or normal subjects. If the ITA value of the sample is greater than the $50^{th}$ percentile, there would be a significant chance that the woman is pregnant, the fetus of the pregnant mother has Down's syndrome, or that the woman has a trophoblastic disease. Similarly, the ITA value could be compared to the $95^{th}$ percentile of ITA values for a population of normal pregnant women or normal subjects. If the ITA value from the sample was greater than the $95^{th}$ percentile, the relative likelihood would be even greater that the woman is pregnant, the fetus of the pregnant woman being tested had Down's syndrome, or that the woman has a trophoblast disease. Thus, an amount of ITA in the sample that is higher than a standard ITA amount may indicate the presence of Down's syndrome in the fetus of the pregnant woman.

As discussed herein, in screening for Down's syndrome, when ITA is measured and combined with the pregnant woman's age, the accuracy of measurement is about 80%, for example about 79%, with a 5% false positive rate. The accuracy of detecting Down's syndrome may improve when the methods of the invention are practiced with one or more additional markers. Some examples of markers that may be employed in conjunction with ITA in practicing the methods of the invention, include, but are not limited to, free hCG, beta-submit hCG, beta-core hCG, unconjugated estriol (UE3), alpha-fetoprotein (AFP), leptin, prorenin, renin, DHEA-S, leukocyte acid phosphatase, inhibin, pregnancy associated plasma protein A (PAPP-A), AFP-L3, P43, superoxide dismutase (SOD), proMBP, fetal DNA, insulin-like growth factor binding proteins 3 (IGFBP3), CA 125, placental lactogen, Hp2FF, serum sialytransferase, s100b protein, schwangers chafts protein 1 (SPI), activin A/follistatin, fetal antigen (FA-2) and placental alkaline phosphatase (PALP). The methods may also be practiced by using ultrasound screens in conjunction with the ITA screens. Likewise, these additional pregnancy markers may be screened with ITA in pregnancy screens or trophoblastic disease screens. In addition, the methods may be practiced by combining results of pregnancy screens obtained separately at different times of pregnancy. For example, the results of an ultrasound screen performed during the first trimester of pregnancy may be combined with the results of an ITA screen performed later during the first trimester, or performed during the second trimester of pregnancy.

For example, when ITA is combined with AFP, and the woman's age, the detection rate may be about 85% with a 5% false positive rate. When ITA is combined with UE3, inhibin, and woman's age, the detection rate may be about 90% with a 5% false positive rate. When ITA is combined with UE3, hCG, inhibin, and AFP, the detection rate may be about 95% with a 5% false positive rate.

In practicing the sandwich immunoassay of the invention, ITA is exposed to at least one capture antibody and may also be exposed to a detection antibody that is coupled to a detectable label. Examples of suitable labels are described above, one example of a label is an acridinium ester. Methods of coupling labels to antibodies are well known in the art. For example, acridinium, as a "sulfonyl chloride ester" can be crosslinked to the detection antibody by the reaction of the lysly moiety of the epsilon amino group of lysine in proteins, such as antibodies, to the acridinium ester. The reaction products may then be separated by size exclusion chromatography on Sepharose beads. One detection antibody is designated B207. B207 was developed to the hCG β fragment as described in Krichevsky et al., (1994) The Development of a Panel of Monoclonal Antibodies to Human Luteinizing Hormone and its Application to Immunological Mapping and Two-Site Assays, Endocrine, 2:511-520.

Although specific monoclonal antibodies are disclosed herein, other monoclonal antibodies that could be used as capture and detection antibodies for ITA as described herein can be produced using conventional methods known in the art. See, for example, Kohler and Milstein, (1975) Nature, 256:495-97; or Sambrook et al. (2001) Molecular Cloning: A Laboratory Manual, 3rd edition, Cold Spring Harbor Laboratory Press. Briefly, animals, such as mice, are injected with an antigen, such as ITA, or fragments thereof, may be coupled to a carrier protein. The animals are boosted with one or more antigen injections, and are hyperimmunized by an intravenous (IV) booster about three days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize different epitopes of the antigen are identified, cultured, and subcloned using standard immunological techniques. The antibodies are then screened for the desired specificity or cross reactivity using methods known in the art.

Although one embodiment of the invention employs chemiluminescent sandwich immunoassays to practice the methods of the invention, other immunoassays, such as ELISAs and RIAs may be used. The parameters and components of the assays are determined and optimized as is well known to those skilled in the art such that the assays provide measurement of ITA levels in the biological samples being assayed. In addition, although certain embodiments of the invention utilize antibodies as the agents capturing the ITA, ITA may be captured in the assays of the invention using other chemical agents or molecules that are not antibodies. For example, such an agent may recognize carbohydrate profiles of ITA, and thereby bind the ITA to a solid phase in a similar manner as the capture antibodies described herein.

In practicing the methods of the invention, conventional techniques for performing the methods can be used. However, in some embodiments it may be desirable to automate the methods as much as practical in order to improve replicability of the results and reduce the time and costs required to conduct the assays. Automated assays used to practice the methods of the invention permit users to conduct at least about 80 tests per hour, and preferably more than about 100 test per hour.

The Nichols Advantage® immunoassay system is a fully automated chemiluminescent system. The system is a benchtop instrument that performs solid phase chemiluminescent immunoassays. Steptavidin-coated magnetic particles and biotinylated antibodies may be employed in the assay system. Acridinium ester is the chemiluminescence label typically used for signal detection. The Advantage immunoassay system has the flexibility to use different formats, optimizing incubation time for each individual assay. The system supports three different assay formats: 1) a simultaneous assay format in which antibodies and solid phase are incubated with the samples at the same time; 2) a sequential assay format in which antibodies are incubated with the samples, streptavidin-coated magnetic particles are added, followed by a further incubation step; and 3) a two step assay format that involves binding of one antibody and the solid phase to the antigen followed by a wash step, and the addition of labeled antibody followed by a second incubation. Other features of the system include on board refrigeration, primary tube sampling, automatic clot and bubble detection, and ready to use reagent cartridges.

The methods of the invention may be practiced using any automated immunoassay system. One may also use any conventional, non-automated, assay device to practice the methods of the invention. For example, a conventional microtiter plate can be used to store the various solutions used in performing the assay. The device should permit the biological sample to be exposed to a combination of antibodies. The antibodies should recognize different epitopes of the antigen(s) being assayed. The device should also cause the bound antigen to be retained to a substrate as solutions are added and removed during the assay.

By way of example, and not by way of limitation, wells of a microtiter plate can be loaded with a solution containing streptavidin coated magnetic particles, as described herein. A solution containing biotin coupled capture antibodies (e.g., biotin coupled B152 mAb) is added to the well to enable the coupling of the capture antibodies to the magnetic particles. A concentration of capture antibody is empirically selected (based on expected antigen concentrations) as discussed herein, to permit binding of all, or essentially all, of the test is antigen that is available in the sample. In that regard, typical antigen concentrations in biological samples are in the nanogram to low microgram range (e.g. 1 ng/ml-5 µg/ml) so that the capture antibody concentrations are in the low to high microgram range (e.g. 1-100 µg/ml). The sample is added to the well. If the sample contains the antigen of interest (e.g., ITA), the antigen will bind to the capture antibodies. The plate is exposed to a magnetic field to immobilize the magnetic particles, and the solution is removed from the well; but the antigen will not be removed because it is bound to the antibodies that are bound to the magnetic particles that are immobilized by the magnetic field. A solution containing the detection antibody coupled to a label (e.g., acridinium labeled B207 mAb) is added to the well containing the bound antigen. As indicated elsewhere herein, the concentration of the detection antibody is preferably selected so that all, or essentially all, of the test antigen molecules (e.g., ITA) are bound by the detection antibody. Thus, the detection antibody can be provided at concentrations at least an order of magnitude greater than the expected concentration of the test antigen. For example, if a test antigen has an expected concentration of 100 ng/ml, the detection antibody concentration can be 1000 ng/ml (1 µg/ml). After a sufficient amount of time (from about 10 minutes to about 8 or more hours), determined and optimized empirically as described herein, the plate is exposed to a magnetic field, the solution is then removed, and the sample is washed. The amount of label remaining in the well is then measured (e.g., by a luminometer). The measured values can be quantitative or qualitative. Quantitative results are usually preferred. The measured values may then be compared to a standard or a threshold.

In practicing the methods of the invention, a control may be provided in the assay to ensure that the reactions have been successful. For example, a control could be provided with a polyclonal antibody solution for other analytes present in the biological sample. A specific example of an analyte is progesterone, or metabolites thereof, in the sample. Another example of a control would be to provide a polyclonal antibody solution that raised against the animal used to produce the monoclonal detection antibodies. For example, if a mouse was used to generate the monoclonal detection antibody, a polyclonal anti-mouse serum, could be used as a control. If the methods are practiced and the test results for the sample and the control are negative, or if the sample is positive and the control is negative (e.g., there is no detectable signal), it is likely to indicate that the woman was either not pregnant to begin with, that an error has been made in the testing protocol, or that the test materials have been compromised in some manner. Alternatively, if a signal is detected in the sample reaction zone and in the control, it is likely that the woman is pregnant.

The methods of the invention may be practiced with diagnostic kits. The diagnostic kits may comprise a capture antibody solution and a detection antibody solution. As disclosed herein, the capture antibody solution may comprise at least one capture antibody that specifically binds ITA. Examples of preferred capture antibodies include monoclonal antibodies B152, clone 820, and clone 827. The detection antibody solution may comprise a monoclonal antibody that binds ITA at a different epitope bound by the capture antibodies. In one embodiment, the detection antibody is an antibody that binds the beta subunit of ITA. For example, the detection antibody may be a monoclonal antibody designated B207.

The diagnostic kits of the invention may be configured for professional (e.g., clinical) or personal use. In one embodiment, the kits of the invention are configured to be used for chemiluminescent assays as described herein. In that regard, the kits employ a signal detection device that is able to detect a signal produced by a chemiluminescent label coupled to the detection antibody. In a certain embodiment of the invention, the signal detection device is a luminometer. The luminometer measures the amount of light emitted from the chemiluminescent label. However, other signal detection devices may be used in the diagnostic kits of the invention. For example, the device may comprise a light bulb that emits light if the amount of signal produced by the chemiluminescent label corresponds to a concentration of antigen that exceeds a particular threshold, as described herein.

Professional kits may be provided to be utilized in automated assay systems as disclosed herein. One example of an automated assay system is the Nichols Advantage® system. A kit for such systems may comprise a plurality of reagent containers designed to retain and store the various solutions used in the methods of the invention. For example, a reagent container can be provided for the capture antibody solution, the detection antibody solution, a magnetic particle solution, and/or one or more wash solutions Reagent containers include any device that can contain a liquid, and permits removal of the liquid therefrom. Examples of reagent containers include, but are not limited to, vials, test tubes, wells, or flasks.

For clinical settings that do not have an automated assay system on sight, a kit may be provided for collecting the sample to be shipped to a laboratory for use in an automated system. In that regard, the kit may comprise a container, such as a vial, for storing the sample.

The foregoing kits may also be provided with tools to assist in the collection of biological samples. Some examples of tools include sample containers, such as vials or cups; needles and syringes for blood or serum samples; antiseptic prepatory pads; gauze pads; and/or swabs for tissue samples.

Personal diagnostic kits are also provided. One example is a "home pregnancy kit". These kits may be configured to permit a person to determine whether she is pregnant, whether she may be pregnant with a fetus with Down's syndrome, or whether she has a trophoblastic disease. In certain embodiments, urine samples may be used in personal diagnostic kits. In an embodiment in which the assay is a chemiluminescent immunoassay, the diagnostic kit may comprise a plurality of reagent containers, a capture antibody solution, and a detection antibody solution. In one embodiment, the kit includes a cup for obtaining the biological sample, and a device, such as a pipette, to transfer a portion of the sample to the assay device. After the sample is inserted into the assay device, it will be exposed to the capture antibody solution, and detection antibody solution. A signal will then be measured, and the woman will be able to determine whether she tested positive for the condition being tested. The device also may contain a control to indicate that the assay was not defective. An example of a control would be a polyclonal antibody solution that detects an analyte commonly found in the type of sample being tested. One example of an analyte is progesterone.

In other embodiments, the label produces a color if the antigen is present in the sample. The presence of a color will be indicative that the woman is positive for the condition being tested.

The following examples are presented to illustrate assays and methods used for detecting ITA in biological samples. The methodology and results may vary depending on the parameters of the assays being used, as well as the antigens being screened. The examples are not intended in any way to otherwise limit the scope of the invention.

EXAMPLES

Example 1

ITA Chemiluminescent Assay

The methods set forth below were performed on a Nichols Advantage® assay system (Nichols Institute Diagnostics (NID), San Juan Capistrano, Calif.).

A series of solutions are provided and stored in individual vials or containers, as described herein. An assay buffer solution comprises 4% protease-free bovine serum albumin (BSA) in 0.5 M phosphate buffer saline (PBS; pH 7.6). A capture antibody solution comprises 4.2 µg/mL (or 0.42 µg/test) of biotin-coupled capture antibody (B152), 0.5% protease free BSA in 0.5 M PBS, 6% normal mouse serum, and 0.1% mouse gamma globulin at a pH of 7.4. A magnetic particle solution comprises 4 mg/mL of steptavidin coated magnetic particles (M-270; Dynal Biotech, Inc., Lake Success, N.Y.) in normal mouse serum. A detection antibody solution comprises about 0.1 µg/test of an acridinium ester-labeled detection antibody (B207), 0.4% BSA in 0.1 M PBS at a pH of 6.0. A wash solution comprises a detergent, such as Tween®, in PBS with 0.1% sodium azide as a preservative.

The assay was performed by adding 15 µL of a sample or a standard (such as an ITA standard), 260 µL of the assay buffer, 70 µL of the capture antibody solution, and 25 µL of the magnetic particle solution to a well in a plate or cuvette. The solution was allowed to incubate for 30 minutes at 37 degrees C.

After incubation, the plate was exposed to a magnetic field to immobilize the ITA/capture antibody/magnetic particle complex. The supernatant was removed and the well was washed with the wash solution. After sufficient washing, determined and optimized empirically, the plate was removed from the magnetic field, and 50 µL of the detection antibody solution and 250 µL of the normal mouse serum was added to the well. The solution incubated for about 10 minutes at 37 degrees C. Subsequently, the plate was again exposed to a magnetic field to immobilize the detection antibody/ITA/capture antibody/magnetic particle complex. The supernatant was removed and the well was washed. An acid solution comprising hydrogen peroxide in a diluted acid, such as HCl, and a base solution comprising diluted sodium hydroxide were then added to the well to trigger the signal of the acridinium ester. The amount of detected signal was then measured in a luminometer, and the data were recorded. If the detected signal exceeded the sensitivity range of the assay, the sample was diluted with a diluent comprising 0.1% protease free BSA in 0.5 M PBS at pH of 7.4.

Figure 2A:
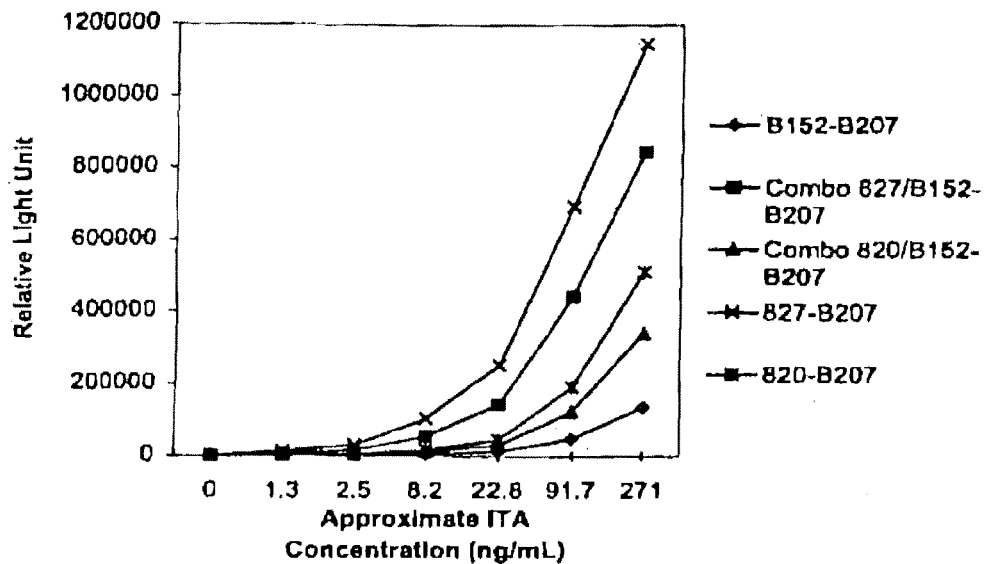
FIG. 2 depicts graphs of relative light unit versus approximate ITA concentration (ng/mL).
FIG. 2B is a magnified version of FIG. 2A depicting the data at ITA concentrations of approximately 0 ng/mL and approximately 1.3 ng/mL. The data are from five assays as described in Examples 1-3, infra. The symbols represent assays of specific capture antibody-detection antibody combinations. The closed diamonds (♦) represent the B152-B207 assay. The closed squares (■) represent the combination assay of clone 827/B152-B207. In particular, the monoclonal antibodies, clone 827 and B152, were the capture antibodies; and the monoclonal antibody B207 was the detection antibody. The closed triangles (▲) represent the combination assay of clone 820/B152-B207. The 'x' (x) represent the clone 827-B207 assay. In particular, the monoclonal antibody, clone 827, was the capture antibody and the monoclonal antibody B207 was the detection antibody. The asterisks (*) represent the clone 820-B207 assay.
Figure 2B:
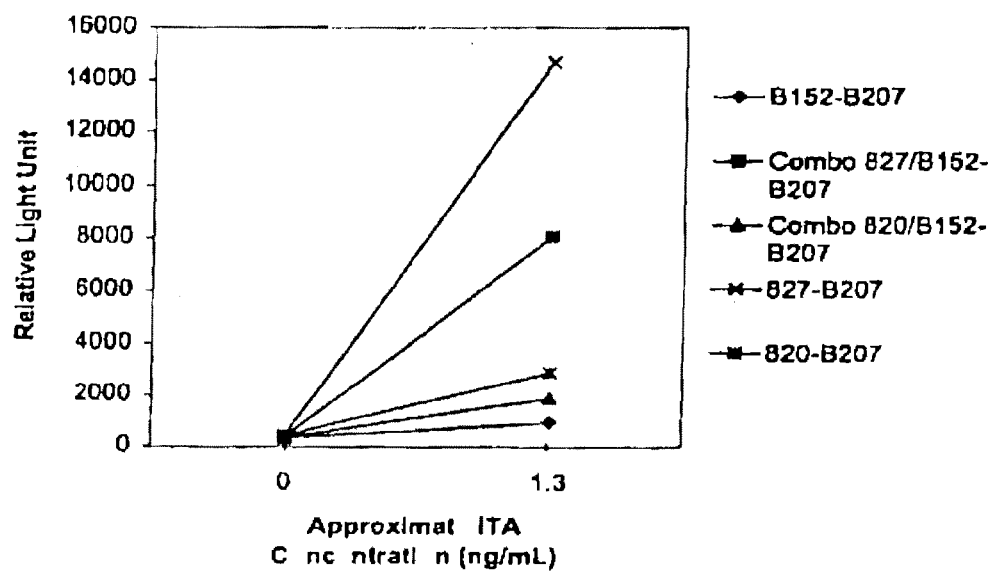

The assay was calibrated using six ITA standards. The ITA standards had ITA concentrations of about 1.3 ng/mL; about 2.5 ng/mL; about 8.2 ng/mL; about 22.8 ng/mL; about 91.7 ng/mL; and about 271 ng/mL. The calculated relative light units (RLU) for each standard were 914 RLU; 1,630 RLU; 4,873 RLU; 12,794 RLU; 48,149 RLU; 135,384 RLU, respectively. The baseline RLU (i.e., when the ITA concentration was 0 ng/mL) was 314 RLU. The results of this assay are depicted in FIGS. 2A and 2B designated by the closed diamond (♦).

A urine sample of a woman was screened for ITA, as described above. The urine sample had a detectable signal of 1,095 RLU. Based on the ITA standard data, this correlated to an ITA concentration of 1.6 ng/mL.

Example 2

ITA/Intact hCG Assay

A combination assay ("combo" assay) was also performed using the B152-B207 assay described in Example 1; however, an additional capture antibody raised against intact hCG was added to the well during the first incubation with the B152 capture antibody and the ITA. The antibody used was designated clone 820 (purchased from Biodesign International, Saco, Me.; Cat. No. E45550M). This assay is referred to herein as the "combo 820/B152-B207" assay. In particular, in this combo assay, the capture antibodies are the clone 820 and the B152 monoclonal antibodies, and the detection antibody is the B207 monoclonal antibody. The results of this assay are illustrated in FIGS. 2A and 2B designated by the closed triangle (▲).

Unexpectedly, the detected signal of ITA appeared to be substantially greater than the detected signal using the B152-B207 assay alone. In that regard, the six ITA standards yielded signals of 1,850 RLU (1.3 ng/mL ITA); 3,178 RLU (2.4 ng/mL ITA); 10,940 RLU (8.4 ng/mL ITA); 31,119 RLU (23.1 ng/mL ITA); 123,118 RLU (90.0 ng/mL ITA); and 341,532 RLU (271.8 ng/mL ITA).

These results appear to indicate that the combo assay 820/B152-B207 provides about 2 to 3 times greater sensitivity than the B152-B207 assay alone. Therefore, it will be possible to detect smaller concentrations of ITA in biological samples at earlier time points than possible by currently available assays.

It is also notable that an assay utilizing the purified monoclonal antibody clone 820 alone appeared to result in greater detectable signals than the combo assay 820/B152-B207 or the B152-B207 assay. The results are indicated in FIGS. 2A and 2B designated by the asterisk (*). The 820-B207 assay appears to be approximately 3 to 4 times more sensitive than the B152-B207 assay.

Example 3

ITA/Free Beta hCG Assay

A combination assay ("combo" assay) was also performed using the B152-B207 assay described in Example 1; however, an additional capture antibody to free beta hCG was added to the well during the first incubation with the B152 capture antibody and the ITA. The antibody used was designated clone #827 (purchased from Biodesign international, Saco, Me.; Cat. No. E45575M). This assay is referred to herein as the "combo 827/B152-B207" assay. In particular, in this combo assay, the capture antibodies are the clone 827 and the B152 monoclonal antibodies, and the detection antibody is the B207 monoclonal antibody. The results of this assay are illustrated in FIGS. 2A and 2B designated by the closed square (■).

Even more unexpectedly, the detected signal of ITA appeared to be substantially greater than the detected signal using the B152-B207 assay alone, or the combo 820/B152-B207 assay. In that regard, the six ITA standards yielded signals of 8,033 RLU (1.3 ng/mL ITA); 16,957 RLU (2.5 ng/mL ITA); 55,264 RLU (8.2 ng/mL ITA); 142,512 RLU (22.9 ng/mL ITA); 441,900 RLU (92.2 ng/mL ITA); and 842,974 RLU (267.9 ng/mL ITA).

These results indicate that the combo assay 827/B152-B207 appears to provide about 6 to 12 times greater sensitivity than the B152-B207 assay alone. Therefore, it will be possible to detect smaller concentrations of ITA in biological samples at earlier time points than possible by currently available assays.

It is also notable that an assay utilizing the purified clone 827 alone appeared to result in greater detectable signals than the combo assay 827/B152-B207 or the B152-B207 assay. The results are indicated in FIGS. 2A and 2B designated by the 'x' (x). The 827-B207 assay appears to be approximately 8 to 22 times more sensitive than the B152-B207 assay.

Example 4

Detection of Down's Syndrome During the Second Trimester of Pregnancy

Serum was obtained from pregnant women during their first or second trimester of pregnancy. Some of the samples had been stored at −60 degrees C. for about 3 years.

The methods were practiced as described in Example 1 using serum as the biological sample.

Figure 3:
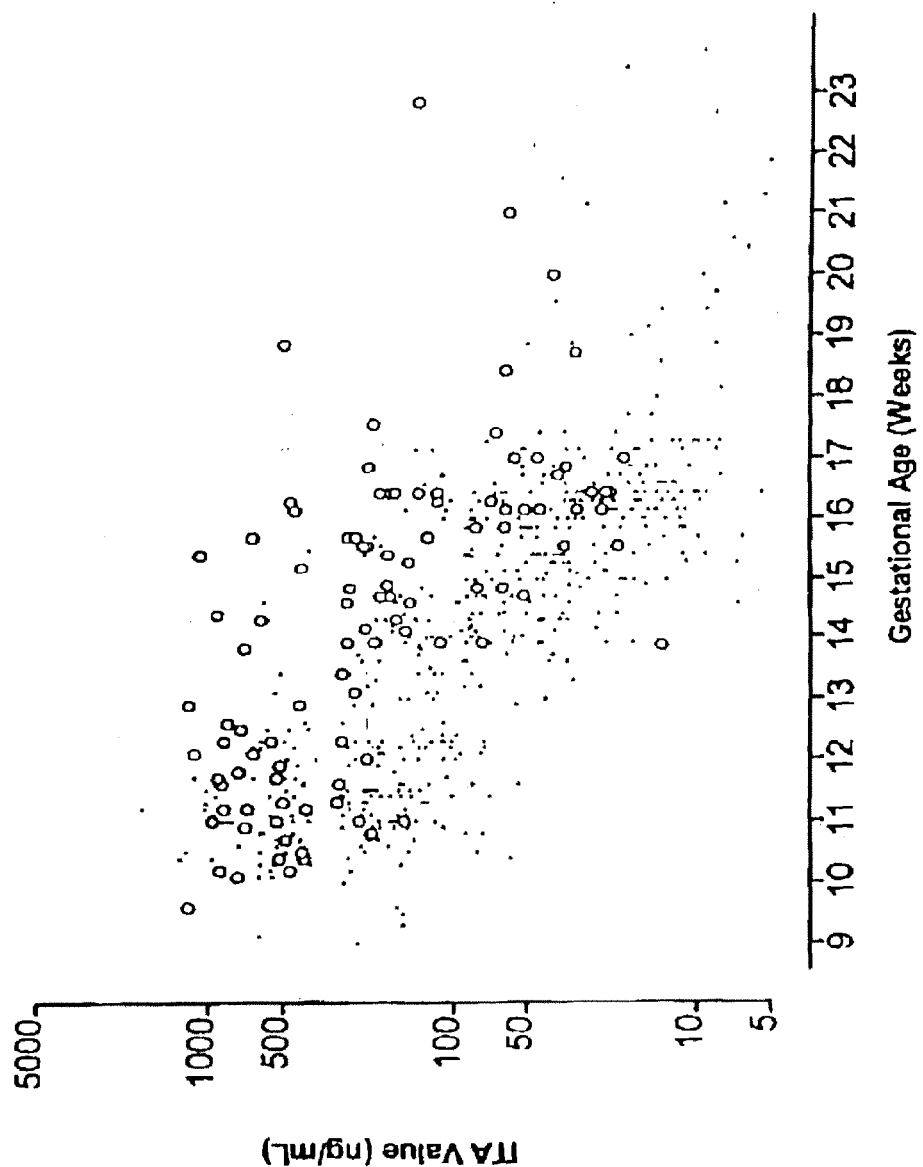
FIG. 3 is a graph of serum ITA concentration (ng/mL) versus gestational age (weeks). Open circles (○) represent ITA values from pregnant women who had Down's syndrome fetuses. Solid circles (●) represent ITA values from pregnant women who had normal fetuses.
Figure 4:
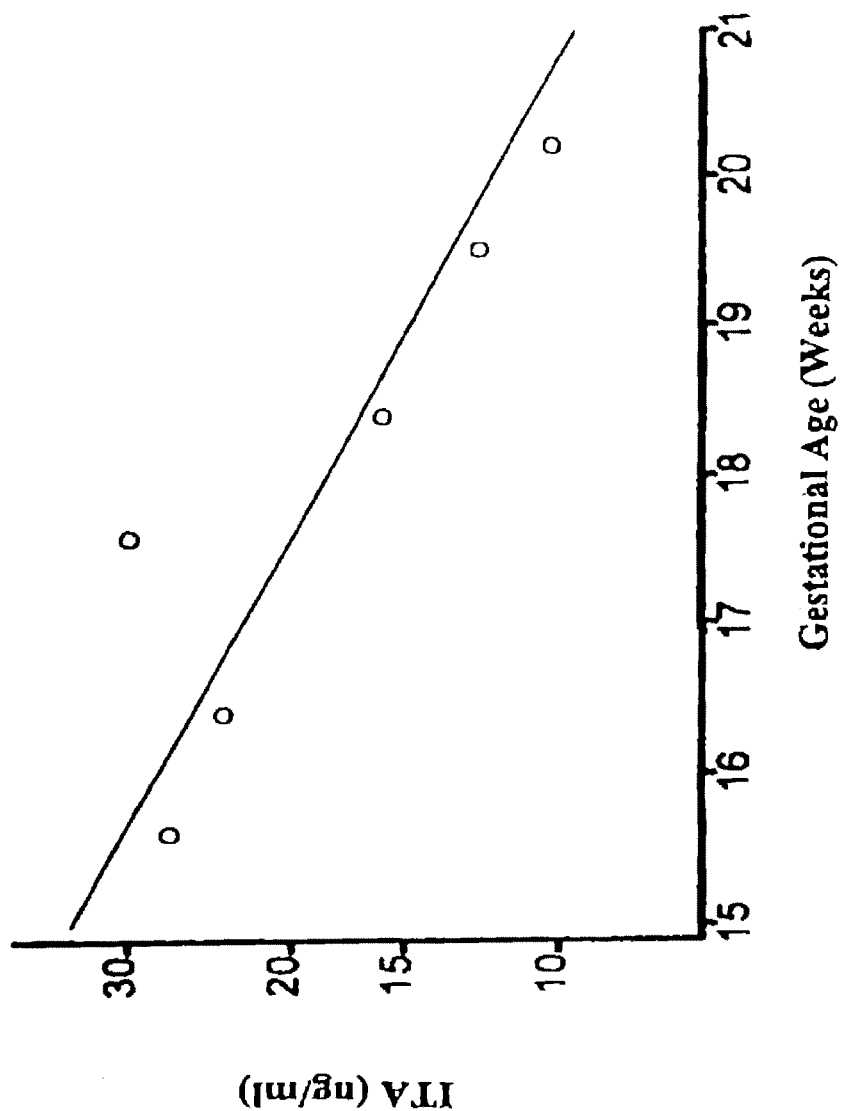
FIG. 4 is a graph of serum ITA concentration (ng/mL) versus gestational age (weeks). The data represent ITA concentrations in serum from pregnant women who had normal fetuses. The data represent the median values of ITA concentration.
Figure 5:
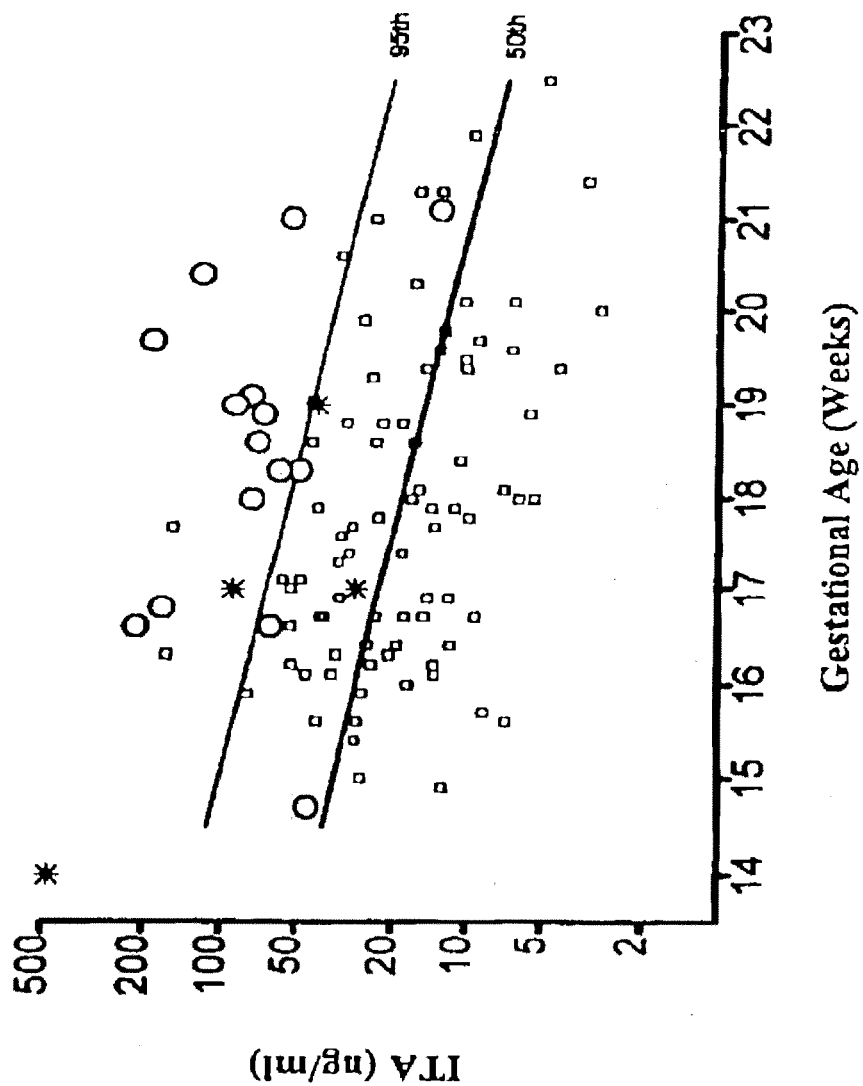
FIG. 5 is a graph of serum ITA concentration (ng/mL) versus gestational age (weeks). Open circles (○) represent ITA values from serum of pregnant women who had Down's syndrome fetuses. Asterisks (*) represent ITA values from serum of pregnant women who had fetuses with Down's syndrome. The serum from these women, in particular, had been frozen and thawed more than once, whereas the serum from the other women (○) had not been frozen and thawed. The open squares (□) represent ITA values from serum of pregnant women who had normal fetuses. The $50^{th}$ and $95^{th}$ percentiles of ITA concentration for normal pregnancies are illustrated as a log Gaussian line fitted for the normal pregnancy values.

Serum ITA values in control pregnancies decreased by about 19% per week during the second trimester (FIGS. 3 and 4). Smoothed median values at 15 and 20 weeks were about 31.0 ng/mL and about 10.7 ng/mL, respectively. When compared to serum ITA data obtained from women with normal pregnancies, differences among the data were observed (FIG. 5). The measured ITA values from serum of women who had fetuses with Down's syndrome (including values from serum that was frozen) were greater than the $50^{th}$ percentile of the ITA values for normal pregnancies. In addition, a significant proportion of the ITA values from the Down's syndrome pregnancies exceeded the $95^{th}$ percentile of the ITA values for normal pregnancies.

Figure 6:
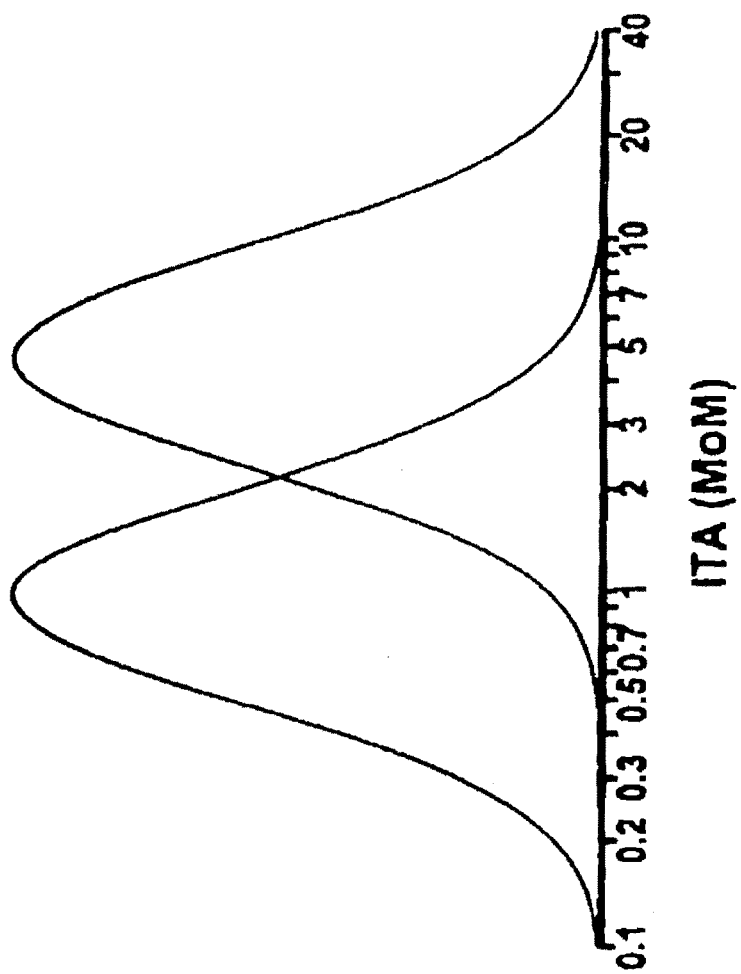
FIG. 6 is a graph of ITA values expressed as Multiples of Medians (MoM) from serum samples obtained from pregnant women who had normal fetuses (curve on the left), and from samples obtained from pregnant women who had fetuses with Down's syndrome (curve on the right).

All results were converted to multiples of the gestational age-specific median (MoM). The normal pregnancies had a median ITA level of 1.02 MoM (FIG. 5). The Down's syndrome pregnancies had a median ITA level of 4.99 MoM (range 1.45 to 15.3 MoM; FIGS. 5 and 6).

Figure 7:
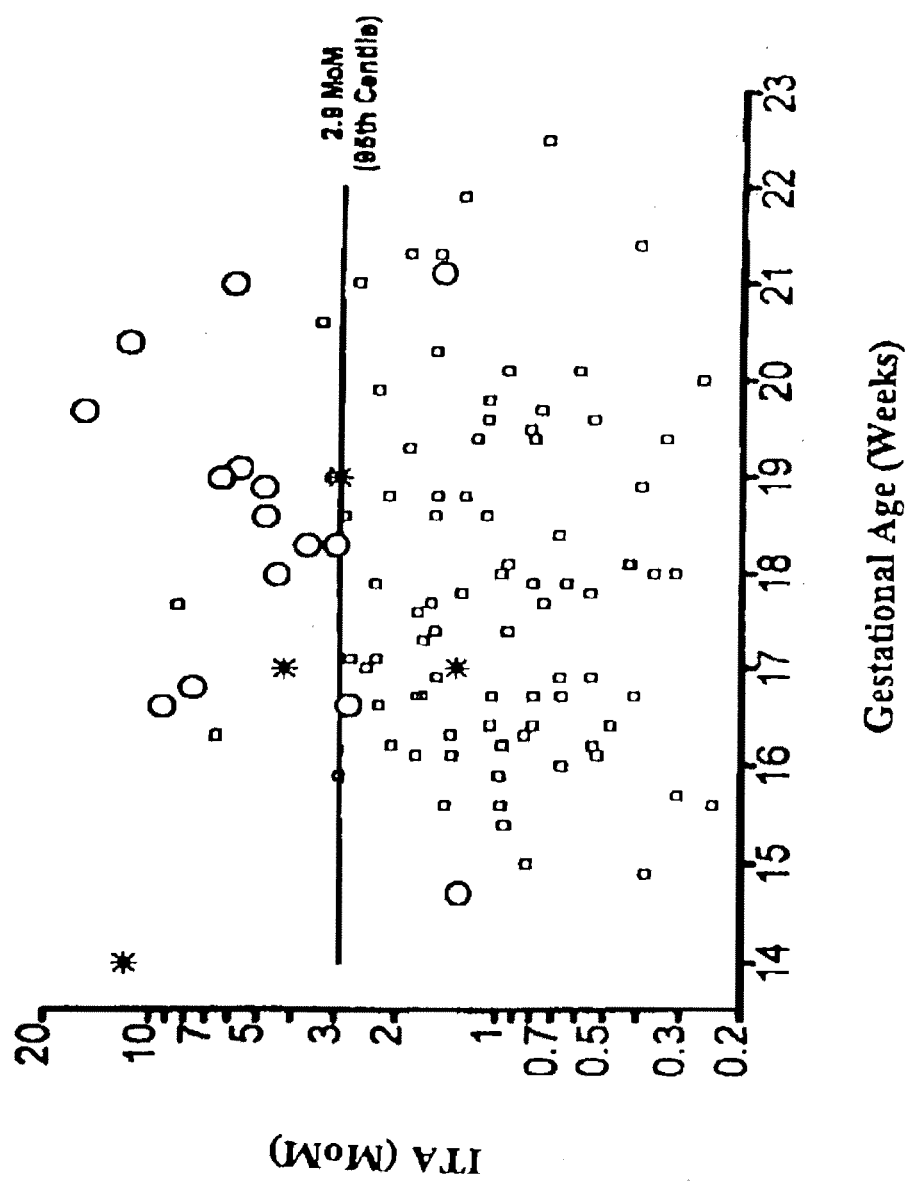
FIG. 7 is a graph of ITA, measured as the "Multiple of Medians" (MoM) versus gestational age (weeks). Open circles (○) represent ITA values from serum of pregnant women who had Down's syndrome fetuses. Asterisks (*) represent ITA values from serum of pregnant women who had fetuses with Down's syndrome. The serum from these women, in particular, had been frozen and thawed more than once, whereas the serum from the other women (○) had not been frozen and thawed. The open squares (□) represent ITA values from serum of pregnant women who had normal fetuses. The $95^{th}$ percentile of ITA (MoM) is indicated as a log Gaussian line.
Figure 8:
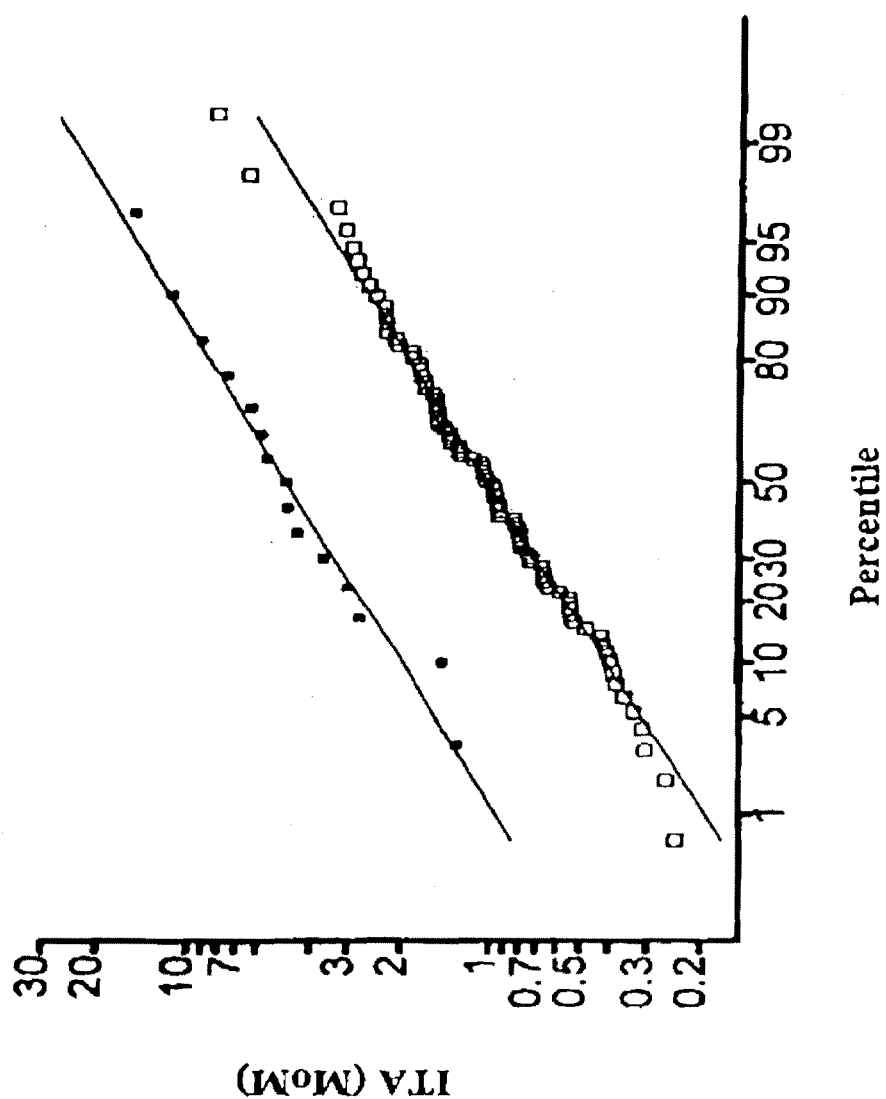
FIG. 8 is a graph of ITA values expressed as Multiples of Medians (MoM) versus percentile. Solid squares (■) represent ITA values from serum samples of pregnant women who had Down's syndrome fetuses. Open squares (□) represent ITA values from serum samples of pregnant women who had normal fetuses.

Overall, about 72% of the Down's syndrome cases were above the $95^{th}$ percentile (2.9 MoM; FIGS. 6 and 7).

When combined with maternal age, detection increased to 79% at a 5% false positive rate. Detection decreased to 72% when the false positive rate is reduced to 3%. Adding α-fetoprotein measurements further increased the detection rate to 87%. For comparison, the most effective combination of markers currently in use (AFP, UE3, hCG, and dimeric inhibin A) can detect 77% of Down's syndrome cases at a 5% false positive rate. In a multivariant analysis using serum ITA, hCG, AFP, UE3, and inhibin-A, the sensitivity was 96% with a 5% false positive rate, 92% with a 3% false positive rate, or 85% with a 1% false positive rate.

Examples of detection rates for various combinations of markers and false positive rates are set forth in Table I below:

TABLE I

| Age and Marker(s) | False Positive Rate | | |
|---|---|---|---|
| | 5% | 3% | 1% |
| ITA | 79% | 72% | 56% |
| ITA & AFP | 87% | 77% | 63% |
| ITA, UE3, hCG, & AFP | 83% | 79% | 63% |
| ITA, UE3, Inhibin | 89% | 82% | 66% |
| ITA, UE3, hCG, Inhibin, & AFP | 96% | 92% | 85% |

Based on these results, second trimester serum ITA levels are about five times higher in Down's syndrome pregnancies than in unaffected pregnancies.

Example 5

Detection of Down's Syndrome During the First Trimester of Pregnancy

Urine samples were obtained from pregnant women during their first trimester of pregnancy. The urine samples were analyzed for ITA, β-core fragment, and hCG, using the method of Example 1. The urine samples were normalized for creatinine. Serum values for total hCG, pregnancy associated plasma protein A, and free beta hCG for these pregnancies were used for multivariate analyses.

Univariately, the median urine ITA levels in the first trimester was about 3.16 MoM as compared to 2.52 MoM for urine hCG, and 1.50 MoM for urine β-core fragment. The observed detection rate for urine ITA at a false positive rate of 5% was 25%. The observed detection rate for urine ITA at a false positive rate of 10% was 53%. These results were is somewhat similar to urine hCG (24% at a 5% false positive rate; and 53% at a 10% false positive rate). The results of urine ITA were better than urine β-core fragment (6% at a 5% false positive rate; and 24% at a 10% false positive rate).

Multivariately, the most powerful combination of 3 analytes was urine ITA with serum pregnancy associated plasma protein, and serum free β-hCG yielding a detection rate of about 74% with a false positive rate of 3%, and a detection rate of about 81% with a false positive rate of 5%. The detection rate is reduced from about 81% to about 74% when urine ITA is replaced by urine hCG.

Thus, urinary ITA combined with serum free β-hCG, and serum pregnancy associated plasma protein provides a first trimester screening performance comparable to that obtained by second trimester screening with four analytes (i.e., AFP, uE3, hCG, and dimeric inhibin A).

Example 6

A woman five days post ovulation wishes to know if she may be pregnant after having sexual intercourse. She leaves a urine sample with her obstetrician. The sample is assayed for ITA using any one of the assays described in Examples 1-3. The amount of ITA measured in the sample is about 1.0 ng/mL. The obstetrician confirms that the woman is pregnant.

Example 7

A woman undergoing fertility treatment is implanted with at least one embryo resulting from in vitro fertilization. Approximately 3 to 4 days after implantation, the woman provides her physician with a urine sample to determine if the implantation was successful. The sample is screened for ITA. The amount of ITA in the sample is about 0.3 ng/mL. The physician confirms that the woman is pregnant.

Example 8

A woman about seven days post ovulation wishes to know if she is pregnant after having sexual intercourse. She obtains a "home pregnancy kit" utilizing any one of the assays described in Examples 1-3. The kit includes a sample cup, a pipette, and an assay device. The assay device comprises a well for the sample, a reagent container for the capture antibody solution, a reagent container for the detection antibody solution, a reagent container for a control solution, an electronic component to control the operation of the assay, and a signal detector, such as a photographic film, or a light bulb. The signal detector detects signals produced by the assay and is preferably set to detect a signal that corresponds to an ITA concentration greater than about 0.3 ng/mL.

The sample is pipetted into the sample well of the kit. The assay is performed on the sample. The light bulb for the sample does not emit light, but the light bulb for the control solution does emit light. This confirms that the assay was successful, but that she is not pregnant.

Example 9

In another embodiment of the invention, an assay may be conducted as follows. In brief, a 96-well microtiter plate (Nunc Immulon-1; Fisher Scientific) is coated with capture antibody (0.2 mL per well of a solution containing 2.5 mg/L B152 antibody in 0.25 mol/L $NaHCO_3$ and 0.1 mol/L NaCl) by incubation for 16-24 hours at 4 degrees C. Plates are then washed three times with water and blotted dry, and wells are blocked with phosphate-buffered saline, pH 7.4 (Life Technologies), containing 10 g/L bovine serum albumin and 0.4 g/L sodium azide (both from Sigma). After incubation for 1 hour at ambient temperature, plates are again washed three times with water, blotted dry, and used for the assay. The total assay volume is 0.2 mL determined as 0.1 mL of sample or calibrator and 0.1 mL of phosphate-buffered saline containing 1 g/L bovine serum albumin and 0.4 g/L sodium azide. C5 hCG (100% hexasaccharide-type O-inked oligosaccharides), the immunogen for antibody B152, that has been calibrated by amino acid analysis is used as the calibrator. C5 hCG at concentrations of 0, 6, 12, and 24 μg/L is added to quadruplicate wells of the plate. Biological samples (urine or serum) are added at two- and five-fold dilutions. Buffer is added, and the plates are incubated for 4 hours at ambient temperature on an orbital plate shaker. Plates are again washed three times with water and blotted dry. Tracer antibody [0.2 mL of peroxidase-labeled B207 mAb, 1:5000 titer in Tris, pH 7.3 (Sigma) containing 1 g/L bovine serum albumin and 1.9 g/L $CaCl_2.2H_2O$] is added to each well. After an additional 2 hour incubation at ambient temperature on a plate shaker, plates are again washed three times with water and blotted dry.

Finally, 0.2 mL of substrate [3,3',5,5'-tetramethylbenzidine (TMB) reagent (Catalog No. T8665; Sigma) diluted 1:1 with water] is added to each well. After a 15 minute incubation at ambient temperature, the reaction is stopped by the addition of 0.05 mL of 2 mol/L HCl. The plates are read on a microtiter plate reader at 450 nm, and the calibrators are plotted. The points best fit a cubic function, which is used to calculate sample values. Plates include a quality control.

Example 10

Assays for Measuring Creatinine

Results of urine assays disclosed herein may be normalized to spot urine creatinine concentrations to adjust for variations in urine concentration. Creatinine concentration may be determined using a commercial kit, Catalog No. 555A (Sigma), and a microtiter plate adaptation of the protocol. Calibrators (0, 2.5, 1.5, 0.5, and 0.2 g/L creatnine) and urine samples (0.053 mL per well, in triplicate) are added to a 96-well microtiter plate. Alkaline picrate reagent is prepared fresh (5 parts of solution plus 1 part sodium hydroxide) and added (250 mL) to the wells. The plate is incubated 15 minutes at ambient temperature. The absorbance is measured at 492 nm by a plate reader, and the calibrators are plotted. The points best fit a cubic equation, which is used to calculate sample concentrations (g/L) (Cole et al., (1999) Clinical Chemistry, 45:2109-2119).

Alternatively, urine creatinine may be measured with a standard Jaffe reaction procedure. Concentration of an analyte is divided by the creatinine concentration to obtain the normalized analyte concentration (Spencer, (1986) Annals of Clinical Biochemistry, 23:1-25).

Example 11

Assays for Measuring β-Core Fragment

β-core fragment concentrations may be determined by a method similar to that for the ITA assay. The assay may utilize an antibody designated B210 (obtained from Columbia University, New York, N.Y., U.S.A.), and a different calibrator (P13 β-core fragment). The β core fragment assay detects hCG β-core fragment. Although this assay has 100% activity with the hLH β-core fragment calibrator, it has no measurable activity with free hCG or any of the intact-hCG calibrators (Cole et al., (1999) Clinical Chemistry, 45:2109-2119).

Alternatively, β-core fragment levels are determined by the B210 assay, as described previously (Cole et al., (1994) Journal of Clinical Endocrinology and Metabolism, 78:497-499; Isozaki et al., (1997) Prenatal Diagnosis, 17:407-413). This is a two-step sandwich assay. Briefly, microtiter plates are coated with monoclonal antibody B210 (obtained from Columbia University, New York, N.Y., U.S.A.), urine samples are added and β-core fragment extracted. Plates are washed and peroxidase-labeled hCG β-subunit antibody (Bios Specific, Emmerville, Calif., U.S.A.) is added to quantitate bound β-core fragment. After a further wash, substrate is added and peroxidase enzyme activity is measured spectrometrically. Urine samples are diluted with phosphate-buffered saline containing 0.1 percent (w/v) bovine serum albumin (normal dilution buffer) for this assay. Samples are assayed at one or more dilutions, as needed (between 50× and 10,000×). The B210 assay is standardized with pure βcore fragment, purified from pregnancy urine and calibrated by amino acid analysis. The B210 assay detects only β-core fragment, with less than 0.1 percent cross-reactivity with free β-subunit and hCG. Plates include a high- and low-quality control.

Example 12

Assays for Measuring Free hCG

Urine samples may be diluted 1 in 5 with zero diluent prior to analysis (Spencer et al., (1997) Prenatal Diagnosis, 17:525-538). The following protocol is an adaptation of measuring serum free hCG, and only difference is diluting the urine sample 1 in 5. The assay of free β-hCG may be carried out with a solid-phase two-site immunoradiometric assay (ELSA-FbHCG; CIS (UK) Ltd., High Wycombe, Bucks., U.K.) in which the monoclonal antibodies used are raised against sterically remote epitopes on the β-hCG molecule. The cross-reactivity of the antibodies with free α-subunit and with intact hCG is less than about 0.01%. The assay involves a 1-h incubation at room temperature of 100 mL of sample and 200 mL of assay buffer in the coated ELSA tube; this is followed by a washing step, a further 2 hour room temperature incubation with 300 mL of labeled second antibody, and a final washing step. The bound radioactivity is counted in an NE1600 multihead gamma-counter (NE Technology Ltd., Reading, U.K.) and the counts are processed by using the WHO mass action curve-fitting routine (Edwards P R, Ekins R P. Mass action model-based microprocessor program for RIA data processing. In: Hunter W M, Corrie J E T, eds. Immunoassays for clinical chemistry, 2nd ed. Edinburgh: Churchill Livingstone, 1983: 640-52) (Spencer, (1991) Clinical Chemistry, 37:809-814).

Alternatively, the NID Laboratories free β (i.e. free hCG) assay can be used. Although this assay is designed to detect serum free hCG (Macri et al., (1993) Annals of Clinical Biochemistry, 30:94-98), diluting the urine sample as above may work with this assay.

The NID Laboratories free β assay is an enzyme linked immunosorbent assay employing monoclonal and affinity purified polyclonal antibodies. Free β used as standard in the NID free β assay is purchased from UCB Bioproducts (Belgium). All incubations are performed at room temperature on a rotator (200 rpm). Briefly, 20 mL of standard, controls and samples in duplicate are incubated with 100 mL of phosphate buffered saline (PBS) in monoclonal coated 96-well microtiter plates for 30 minutes. After a wash procedure 100 mL of biotinylated polyclonal antibody is incubated in all wells for 30 minutes. After another wash procedure the plates are incubated with 100 mL of streptavidin-horseradish peroxidase conjugate for 4.5 minutes. After a final wash procedure, plates are incubated with 100 mL of ortho-phenylenediamine solution for 8.0 minutes after which the reaction is stopped with 100 mL of 1 N $H_2SO_4$ and the absorbance values are read on a microtiter plate reader. Controls and samples are quantitated from the standard curve (Macri et al., (1993) Annals of Clinical Biochemistry, 30:94-98).

Example 13

Assays for Measuring Total Estriol

Total estriol is determined by radioimmunoassay, using a kit sold by Diagnostic Products Corporation (Los Angeles, Calif., U.S.A.). The kit utilizes antibody-coated tubes, estriol-releasing enzyme, radioiodine-labeled tracer, and a set of six standards (Catalog No. TKE35). The procedures are those described in the instruction booklet. Urine samples are initially diluted to 1 to 31 for the immunoassay. Further dilutions, 1 to 1, 1 to 10, and 1 to 100, are made as needed (Cole et al., (1999) Prenatal Diagnosis, 19:340-350; Cole et al., (1997) Prenatal Diagnosis, 17:1125-1133).

Alternatively, total estriol may be measured in duplicate using the Johnson and Johnson Estriol (total) II radioimmunoassay (Johnson and Johnson Clinical Diagnostics Ltd., Amersham, U.K.). Urine samples are either analyzed without dilution, or are diluted 1 in 5 in normal female serum.

In another assay, levels of total estriol may be determined using a specific fluorescence polarization immunoassay (TDx total estriol), Abbott Laboratories, Abbott Part, Ill., U.S.A.). Because of high levels of estriol in pregnancy urine, samples are diluted about 1:100 prior to assay in sample diluent provided with the kit. For total estriol, the 284 and 3647 ng/ml controls have inter-assay coefficients of variations (CVs) of 6.2 and 5.3 percent, respectively, and intra-assay CVs of 4.8 and 3.6 percent, respectively (Kellner et al., (1997) Prenatal Diagnosis, 17:1135-1141).

Various publications and/or references have been cited herein, the contents of which are incorporated herein by reference.

While this invention has been described with respect to various specific examples and embodiments, it is to be understood that the invention is not limited thereto and that it can be variously practiced with the scope of the following claims.

We claim:

1. A method for detecting a trophoblastic disease in a subject comprising the steps of:
    (i) contacting in one assay a biological sample of the subject in a combination assay with at least two capture antibodies that specifically bind different epitopes of invasive trophoblast antigen (ITA) and at least one detection antibody that binds an epitope of the ITA different from the epitopes bound by the capture antibodies, the at least one detection antibody being coupled to a label that is effective to produce a detectable signal;
    (ii) detecting a signal produced by the label when the detection antibody is bound to ITA;
    (iii) confirming that the subject is not pregnant; and
    (iv) determining an amount of ITA present in the biological sample based on the detected signal in step (ii), wherein an amount of ITA greater than about 400,000 ng/ml, indicates the presence of a trophoblastic disease.

2. The method of claim 1, wherein the trophoblastic disease is a choriocarcinoma.

3. The method of claim 1, wherein the trophoblastic disease is a hydatidiform mole.

4. The method of claim 1, wherein the sample is selected from the group consisting of liquid samples, and tissue samples.

5. The method of claim 1, wherein the determining step comprises detecting a signal product by label.

6. The method of claim 5, wherein the signal is a chemiluminescent signal.

* * * * *